United States Patent
Choo et al.

(10) Patent No.: US 9,888,904 B2
(45) Date of Patent: Feb. 13, 2018

(54) HOUSING AND CONNECTOR FOR DOOR USING THE SAME

(71) Applicants: HYUNDAI MOTOR COMPANY, Seoul (KR); Kia Motors Corporation, Seoul (KR); Korea Electric Terminal Co., Ltd., Incheon (KR)

(72) Inventors: Sung Kwan Choo, Hwaseong-si (KR); Jong Soo Kim, Suwon-si (KR); Myung Hoon Kim, Incheon (KR)

(73) Assignees: Hyundai Motor Company, Seoul (KR); Kia Motors Corporation, Seoul (KR); Korea Electric Terminal Co., Ltd., Incheon (KR)

( * ) Notice: Subject to any disclaimer, the term of this patent is extended or adjusted under 35 U.S.C. 154(b) by 249 days.

(21) Appl. No.: 14/673,721

(22) Filed: Mar. 30, 2015

(65) Prior Publication Data
US 2016/0068120 A1 Mar. 10, 2016

(30) Foreign Application Priority Data
Nov. 7, 2014 (KR) .................. 10-2014-0154689

(51) Int. Cl.
| | | |
|---|---|---|
| *H01R 13/502* | (2006.01) | |
| *B60R 16/02* | (2006.01) | |
| *A61B 8/00* | (2006.01) | |
| *B60R 16/03* | (2006.01) | |
| *B06B 1/06* | (2006.01) | |

(52) U.S. Cl.
CPC .......... *A61B 8/4444* (2013.01); *B06B 1/0622* (2013.01); *B60R 16/0222* (2013.01); *B60R 16/03* (2013.01); *H01R 13/5025* (2013.01); *A61B 2560/0468* (2013.01); *A61B 2562/166* (2013.01); *B06B 1/0685* (2013.01); *H01R 13/502* (2013.01)

(58) Field of Classification Search
CPC ............ B60R 16/0222; H01R 13/5025; H01R 13/502
USPC ......................... 439/519, 521, 445, 447, 449
See application file for complete search history.

(56) References Cited

U.S. PATENT DOCUMENTS 5,279,507 A 1/1994 Kameyama

FOREIGN PATENT DOCUMENTS

| | | |
|---|---|---|
| JP | 5-334932 A | 12/1993 |
| JP | 7-141949 A | 6/1995 |
| JP | 10-074558 A | 3/1998 |
| JP | 11-144794 A | 5/1999 |
| JP | 2001-251724 A | 9/2001 |
| JP | 2012-084429 A | 4/2012 |
| KR | 10-0622749 B1 | 9/2006 |

(Continued)

*Primary Examiner* — Renee S Luebke
*Assistant Examiner* — Paul Baillargeon
(74) *Attorney, Agent, or Firm* — McDermott Will & Emery LLP

(57) ABSTRACT

The present disclosure relates to a housing and a connector for a door using the same. The housing forming a skeleton of a connector for a door coupled with a counter connector which is mounted in a panel includes: a terminal seating space configured to be formed by penetrating through the housing back and forth and an electric wire seating space configured to communicate with the terminal seating space to be opened to a rear of the housing, and an electric wire guide cover configured to prevent the electric wire seating space from protruding backward so as to prevent a load from being applied to a grommet in which an electric wire is coupled with the housing.

12 Claims, 6 Drawing Sheets

(56) References Cited

FOREIGN PATENT DOCUMENTS

| KR | 10-2009-0043338 A | 5/2009 |
|----|-------------------|--------|
| KR | 10-0921304 B1 | 10/2009 |
| KR | 10-2011-0070192 A | 6/2011 |
| KR | 2014-0092195 A | 7/2014 |

HOUSING AND CONNECTOR FOR DOOR USING THE SAME

CROSS-REFERENCE TO RELATED APPLICATION

This application is based on and claims the benefit of priority to Korean Patent Application No. 10-2014-0154689, filed on Nov. 7, 2014 in the Korean Intellectual Property Office, the disclosure of which is incorporated herein in its entirety by reference.

TECHNICAL FIELD

The present disclosure relates to a housing and a connector for a door using the same, and more particularly, to a housing including a grommet for waterproof and a connector for a door using the same.

BACKGROUND

In a vehicle, a connector for a door for signal connection with a power supply between electric components installed at a door and a main body of the vehicle is used. The connector for a door is coupled with a separate connector which is mounted in a panel and an electric wire from the connector for a door extends into the door, enclosed with a grommet for waterproof.

The connector for a door needs to be positioned in a narrow space between the door and the main body of the vehicle and therefore a protruding degree of the grommet which is mounted at the connector for a door needs to be managed low. However, as illustrated in FIG. 6, and the like of Related Art Document with reference to the existing connector for a door, the electric wire extending from the connector for a door to the outside is bent in a state in which it once extends to a rear of the connector for a door. In such a structure, a length of the electric wire which is connected to a terminal of the connector for a door is increased, such that a cost burden may be increased and transmissibility of a signal may be relatively reduced.

Further, the electric wire more protrudes than a rear end of the housing of the connector for a door and then is bent, and therefore the grommet mounted therein cannot but relatively more protrude from the rear end of the housing of the connector for a door. Therefore, a size of the connector for a door which is used in the narrow space between the main body of the vehicle and the door is increased and thus a freedom of design of the vehicle may be degraded.

Further, the related art is relatively difficult to mount the grommet in the housing. The reason is that a dimension of the grommet is designed to make a portion where the grommet is locked to the housing adhere to the housing for waterproof and the portion where the grommet is locked constantly protrudes to the rear of the housing.

RELATED ART DOCUMENT

Patent Document (Patent Document 1) Korean Patent No. 10-0921304

SUMMARY

The present disclosure has been made to solve the above-mentioned problems occurring in the prior art while advantages achieved by the prior art are maintained intact.

An aspect of the present disclosure is to minimize a M length of an electric wire protruding from a connector for a door used in a vehicle toward a rear end of a housing.

Another aspect of the present disclosure is to minimize a height of a grommet enclosing an electric wire protruding from a connector for a door toward a rear end of a housing.

According to an exemplary embodiment of the present disclosure, a housing forming a skeleton of a connector for a door coupled with a counter connector which is mounted in a panel includes: a terminal seating space configured to be formed by penetrating through the housing back and forth and an electric wire seating space configured to communicate with the terminal seating space to be opened to a rear of the housing, and an electric wire guide cover configured to prevent the electric wire seating space from protruding backward so as to prevent a load from being applied to a grommet in which an electric wire is coupled with the housing.

According to another exemplary embodiment of the present disclosure, a housing forming a skeleton of a connector for a door coupled with a counter connector which is mounted in a panel includes: a terminal seating space configured to be formed by penetrating through the housing back and forth and an electric wire seating space configured to communicate with the terminal seating space to be opened to a rear of the housing, wherein the electric wire seating space is formed to be opened in a direction toward which a rear of the housing and one side of the housing face, and a locking rib is formed to enclose an edge of an inlet of the terminal seating space, a portion opened to the rear of the housing is provided with a parallel part of the locking rib, and an edge of the inlet of the terminal seating space opened to a side of the housing is provided with an inclined part of the locking rib.

According to still another exemplary embodiment of the present disclosure, a connector for a door includes: a housing configured to be provided with a terminal seating space in which a terminal is seated by penetrating through the housing back and forth and provided with an electric wire seating space communicating with the terminal seating space to be opened backward; and a grommet configured to be mounted in the housing to close the electric wire seating space of the housing to prevent external foreign materials from being entered into the electric wire seating space of the housing, wherein the electric wire seating space formed in the housing is formed to be opened in a direction toward which a rear of the housing and one side of the housing face, a locking rib is formed to enclose an edge of an inlet of the terminal seating space, and a portion opened to a rear of the housing is provided with a parallel part of the locking rib and an edge of an inlet of the terminal seating space opened to a side of the housing is provided with an inclined part of the locking rib.

BRIEF DESCRIPTION OF THE DRAWINGS

The above and other objects, features and advantages of the present disclosure will be more apparent from the following detailed description taken in conjunction with the accompanying drawings, in which.

DETAILED DESCRIPTION

Figure 1:
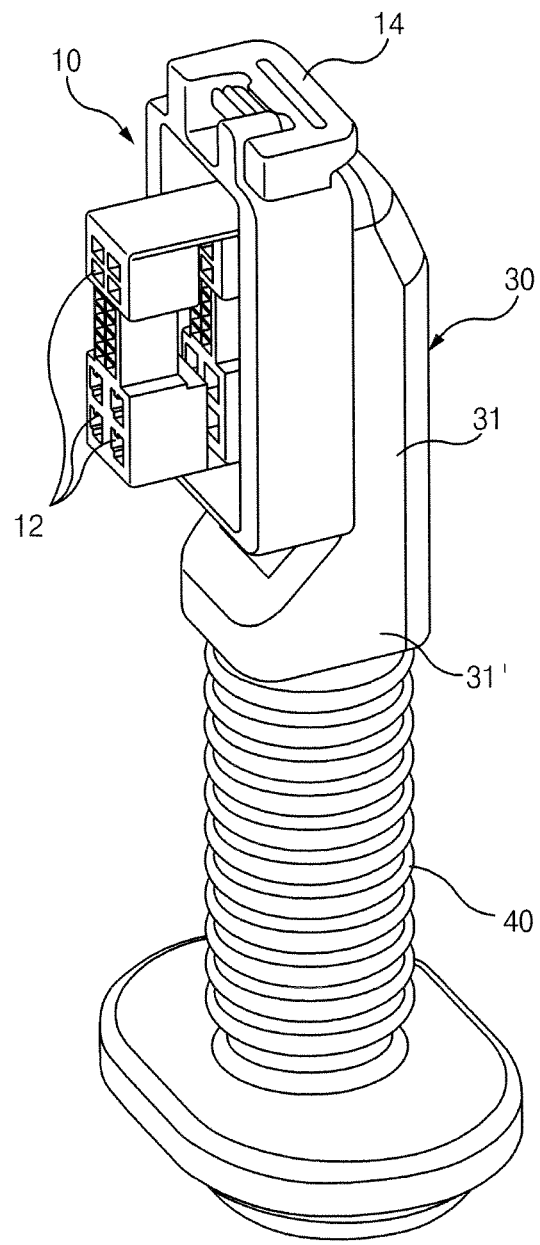
FIG. 1 is a perspective view illustrating a configuration of a connector for a door according to an exemplary embodiment of the present disclosure.
Figure 2:
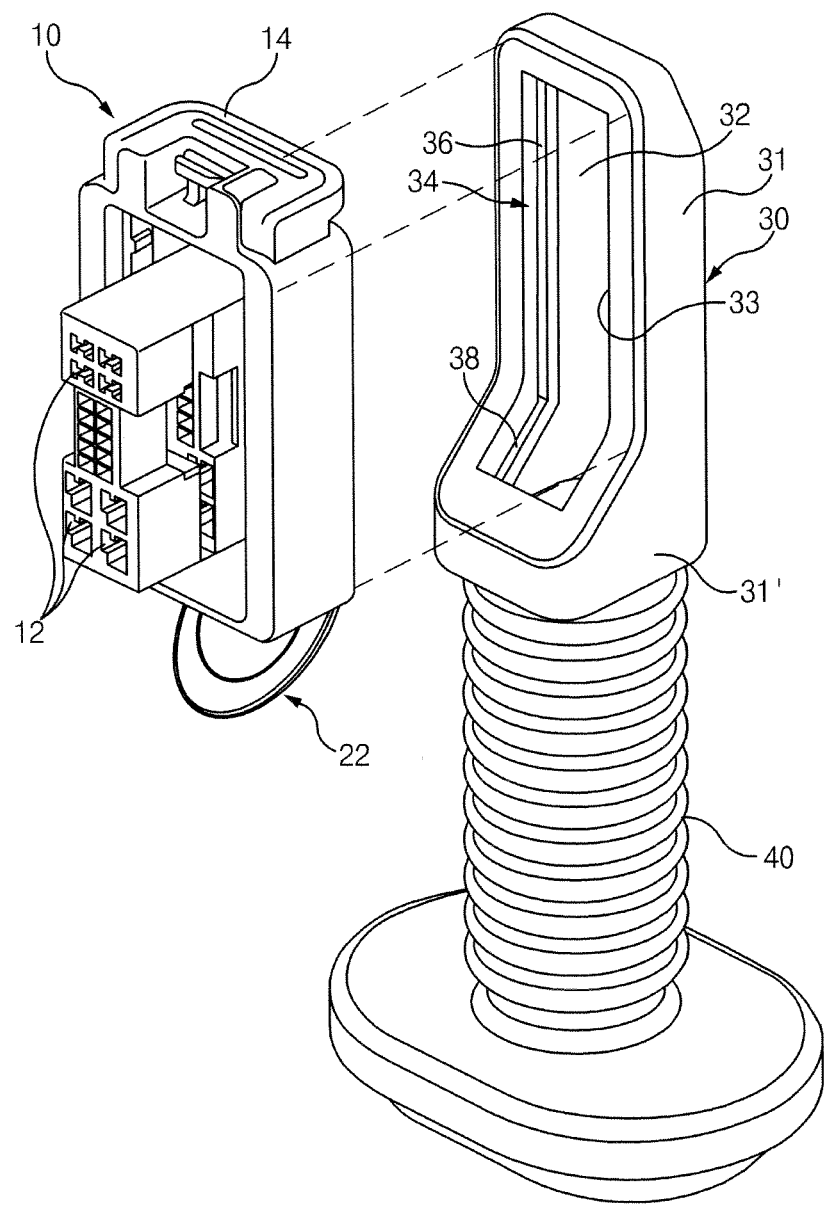
FIG. 2 is an exploded perspective view illustrating a state in which a grommet is separated from a housing of the connector for a door according to the exemplary embodiment of the present disclosure.
Figure 3:
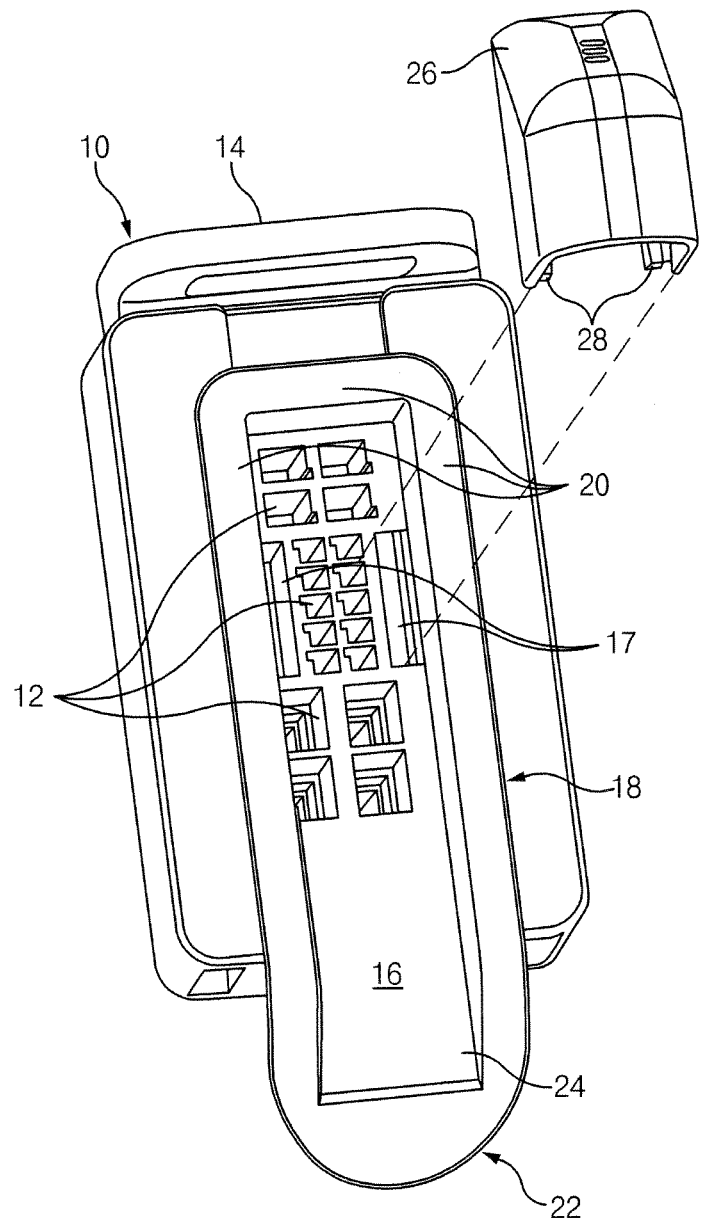
FIG. 3 is a perspective view of the housing according to the exemplary embodiment of the present disclosure viewed from a rear.
Figure 4:
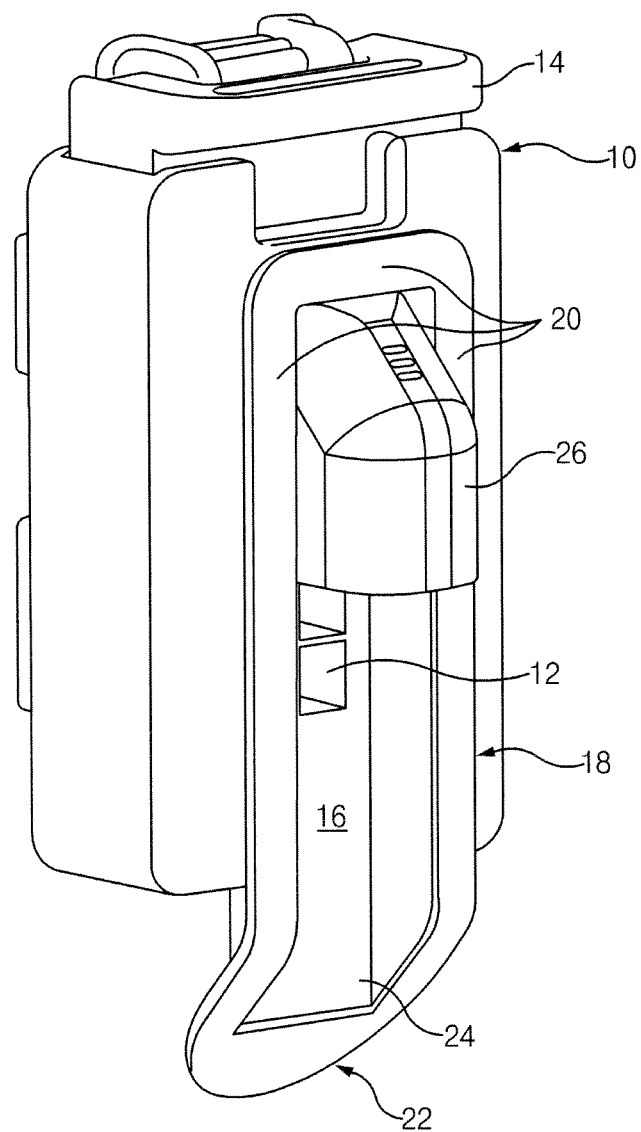
FIG. 4 is a perspective view of a side and a rear side of the housing according to the exemplary embodiment of the present disclosure.

Hereinafter, some exemplary embodiments in the present specification will be described in detail with reference to the illustrative drawings. It is to be noted that in adding reference numerals to elements of each drawing, like reference numerals refer to like elements even though like elements are shown in different drawings. Further, in describing exemplary embodiments of the present disclosure, well-known functions or constructions will not be described in detail since they may unnecessarily obscure the understanding of the present disclosure.

In addition, in describing components of exemplary components of the present disclosure, terms such as first, second, A, B, (a), (b), etc. can be used. These terms are used only to differentiate the components from other components. Therefore, the nature, times, sequence, etc. of the corresponding components are not limited by these terms. When any components are "connected", "coupled", or "linked" to other components, it is to be noted that the components may be directly connected or linked to other components, but the components may be "connected", "coupled", or "linked" to other components via another component therebetween.

As illustrated in the accompanying drawings, a housing 10 determines a skeleton and an appearance of a connector for a door. The housing 10 is made of an insulating synthetic resin. A terminal seating space 12 in which a terminal (not illustrated) is positioned is formed by penetrating through the housing 10 back and forth. In the illustrated exemplary embodiment, a shape and an area of a cross section of the terminal seating space 12 may be variously formed. This is to seat different kinds of terminals.

The housing 10 is provided with a lever 14. The lever 14 is configured to be coupled with a counter connector 60 illustrated in FIG. 6, moving in a direction orthogonal to a length direction of the housing 10. The lever 14 is inclinedly provided with a guide groove and an interlocking protrusion of the counter connector 60 is guided along the guide groove to couple the counter connector 60 with the connector for a door according to the exemplary embodiment of the present disclosure.

A rear end of the housing 10 is provided with an electric wire seating space 16. The electric wire seating space 16 is formed at a rear end of the housing 10 as a concave space. The electric wire seating space 16 is opened to the rear of the housing 10 and is also opened to one of the sides of the housing 10.

A floor of the electric wire seating space 16 is provided with locking holes 17 to which locking pieces 28 of an electric wire guide cover 26 to be described below are locked. A pair of the locking holes 17 is formed in parallel.

A locking rib 18 is formed along an edge at which the electric wire seating space 16 is opened. The locking rib 18 is formed along an edge of an inlet of the electric wire seating space 16. The locking rib 18 is continuously formed to draw a closed curve. As illustrated in the drawings, the locking rib 18 is configured of a parallel part 20 extending to be parallel with a rear surface of the housing 10 and an inclined part 22 extending to be inclined with respect to the parallel part 20. The inclined part 22 is provided so that the electric wire seating space 16 encloses the portion opened to the side of the housing 10.

A leading end of the inclined part 22 of the locking rib 18 has a curved form. This is to well insert the leading end of the inclined part 22 of the locking rib 18 into a locking channel 34 through an inlet 33 of the grommet 30 to be described below.

A portion of which the three surfaces are enclosed with the inclined part 22 of the locking rib 18 is an electric wire extending part 24. The electric wire extending part 24 is a portion where the electric wire present in the electric wire seating space 16 extends to the outside of the electric wire seating space 16. Therefore, the electric wire extending part 24 is opened in a direction toward which one side of the housing 10 faces. For reference, the inclined part 22 of the locking rib 18 forming the electric wire extending part 24 is formed at a portion extending from one side of the housing 10.

The portion of the electric wire seating space 16 which is opposite to the electric wire extending part 24 is locked to the locking hole 17 and thus is provided with the electric wire guide cover 26 which is mounted in the electric wire seating space 16. The electric wire guide cover 26 serves to keep a bent state of the electric wire from the terminal seating space 12 and suddenly bent in the electric wire seating space 16 and to guide a bent direction. The electric wire guide cover 26 is configured to open a surface looking at the terminal seating space 12 and a surface looking at the electric wire extending part 24 and an inner surface thereof is provided with a curved surface having a predetermined curvature radius to guide the bending of the electric wire.

The leading end from the electric wire guide cover 26 toward the terminal seating space 12 is provided with the locking piece 28 which is locked to the locking hole 17. The locking piece 28 is inserted into the locking hole 17, elastically deformed and is recovered from the inserted state to an original state and thus is locked to the locking hole 17.

The grommet 30 is mounted at the rear end of the housing 10 to serve to prevent external foreign materials including moisture from being transferred to the electric wire present at the electric wire seating space 16. The grommet 30 is generally made of a material having good elasticity like rubber. The grommet 30 is mounted on the housing 10, locked to the locking rib 18.

The grommet 30 is provided with a rear end mounting part 31 which is mounted at the rear end of the housing 10 and a side mounting part 31' which is mounted on the side of the housing 10. The rear end mounting part 31 and the side mounting part 31' are integrally formed. When viewed from the front and rear length direction of the housing 10, a length of the rear end mounting part 31 is formed to be shorter than that of the side mounting part 31'.

The front surface of the rear end mounting part 31 is formed to be parallel with the rear surface of the housing 10 and the front surface of the side mounting part 31' extends to be inclined to the front surface of the rear end mounting part 31.

An inside of the grommet 30 is provided with the electric wire seating space 32. The electric wire seating space 32 cooperates with the electric wire seating space 16 of the housing 10 to form a space in which the electric wire is seated. The locking channel 34 in which the locking rib 18 is seated and locked is formed along the inner side of the inlet 33 of the electric wire seating space 32. A shape of the locking channel 34 is formed to correspond to a shape of the parallel part 20 and the inclined part 22 of the locking rib 18. That is, the locking channel 34 is configured of a portion parallel with the rear surface of the housing 10 and a portion formed to be inclined thereto, and a portion corresponding to the inclined part 22 is formed at the side mounting part 31'. The portion of the inlet 33 formed at the side mounting part 31' is formed to have an inclination corresponding to the inclined part 22 of the locking rib 18.

Here, in the locking channel 34, the portion where the parallel part 20 of the locking rib 18 is mounted is a parallel part 36 and is formed to enclose the inner side of the inlet 33 of the rear end mounting part 31. In the locking channel 34, the portion where the inclined part 22 of the locking rib 18 is mounted is an inclined part 38 and is formed to enclose the inner side of the inlet 33 of the side mounting part 31'.

The grommet 30 is connected to a pipe part 40 to communicate with the electric wire seating space 32. The electric wire passing through the electric wire seating space 32 passes through the pipe part 40.

Hereinafter, the use of the housing and the connector for a door using the same according to the exemplary embodiment of the present disclosure having the configuration as described above will be described in detail.

According to the exemplary embodiment of the present disclosure, each of the terminals (not illustrated) is inserted into the terminal seating space 12 of the housing 10 and thus seated. The terminal is connected to the electric wire, in M which the electric wire comes out from the terminal seating space 12 and thus extends to the electric wire seating space 16 of the housing 10. The electric wires from the electric wire seating space 16 come out from the electric wire seating space 16 through the electric wire extending part 24.

The electric wire comes out from the electric wire seating space 16 of the housing 10 through the electric wire extending part 24, and then the electric wire guide cover 26 is mounted in the electric wire seating space 18 of the housing 10. The locking piece 28 of the electric wire guide cover 26 is locked to the locking hole 17 formed in the electric wire seating space 12. In the electric wire seating space 16, the electric wire guide cover 26 guides an electric wire which is at a farthest side from the electric wire extending part 24 to keep the extending state to the electric wire extending part 24. When the electric wire from the terminal seating space 12 extends from the electric wire seating space 16 to the electric wire extending part 24, the electric wires which are at a farthest side from the electric wire extending part 24, that is, the electric wires guided by the electric wire guide cover 26 are at the outermost side and thus serve to press the rest electric wires to some extent.

In this state, the grommet 30 is mounted on the housing 10. First, the electric wire coming out to the outside through the electric wire extending part 24 is put into the electric wire seating space 32 through the inlet 33 of the grommet 30 and thus extends to the opposite side by penetrating through the pipe part 40.

Further, an operation of mounting the grommet 30 on the housing 10 starts. Since the grommet 30 is made of a material having elasticity like rubber, the locking rib 18 of the housing 10 is inserted into the locking channel 34 while the portion of the inlet 33 is elastically deformed.

According to the exemplary embodiment of the present disclosure, in the locking channel 34, the inclined part 22 of the locking rib 18 is first inserted into the inclined part 38. The reason is that the inclined part 38 of the locking channel extends to be inclined to the parallel part 36 of the locking channel 34 and thus the inclined part 22 of the locking rib 18 of the housing 10 may be easily inserted.

Next, when the inclined part 22 of the locking rib 18 is inserted into the inclined part 22 of the locking channel 34 and then the grommet 30 adheres to the housing 10, the rest portion of the inclined part 22 of the locking rib 18 is inserted into the inclined part 38 of the locking channel 34. To be continued, when the grommet 30 is pressed, the parallel parts 20 of the locking rib 18 are sequentially inserted into the parallel parts 36 of the locking channel 34 formed in the grommet 30.

By this, all of the locking ribs 18 of the housing 10 are inserted into the locking channel 34 of the grommet 30 and thus the grommet 30 is mounted on the housing 10, thereby preventing moisture from being transferred from the outside to the electric wire which is present at the electric wire seating space 16.

Figure 5:
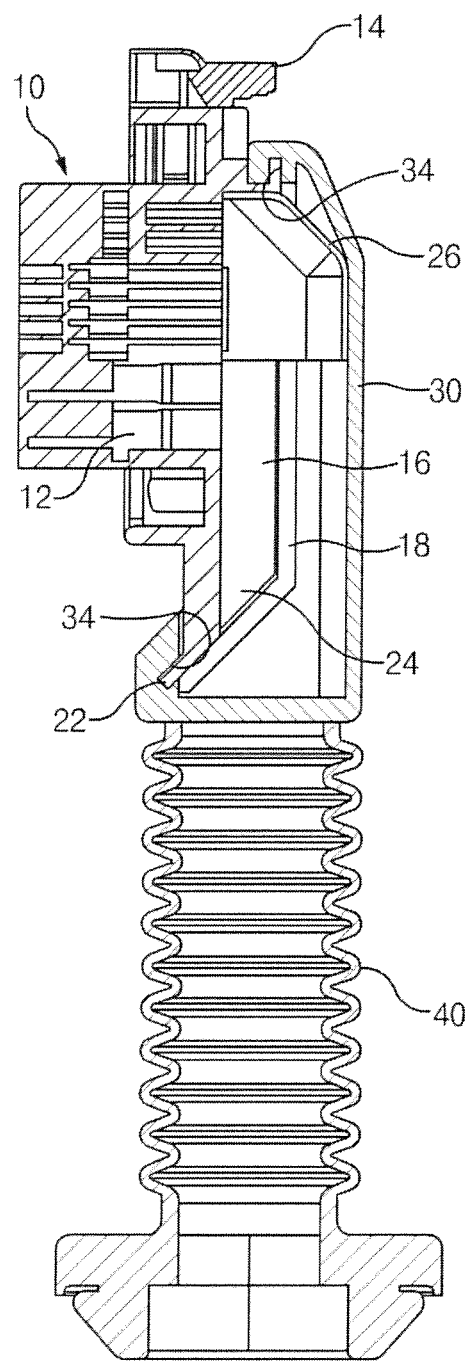
FIG. 5 is a cross-sectional view illustrating a configuration of the connector for a door according to the exemplary embodiment of the present disclosure.

Meanwhile, it may be appreciated from illustrated in FIG. 5 that the position at which the electric wire extends from the housing 10 is at a position less protruding toward the rear of the housing 10. The reason is that the electric wire is not bent after extending from the electric wire seating space 16 of the housing 10 toward the rear of the housing 10 but is directly bent in the electric wire seating space 16 and thus extends to the outside of the housing 10 through the electric wire extending part 24. That is, since the electric wire extending part 24 is opened in a direction toward which one side of the housing 10 faces, the electric wire less protrudes toward the rear of the housing 10.

Figure 6:
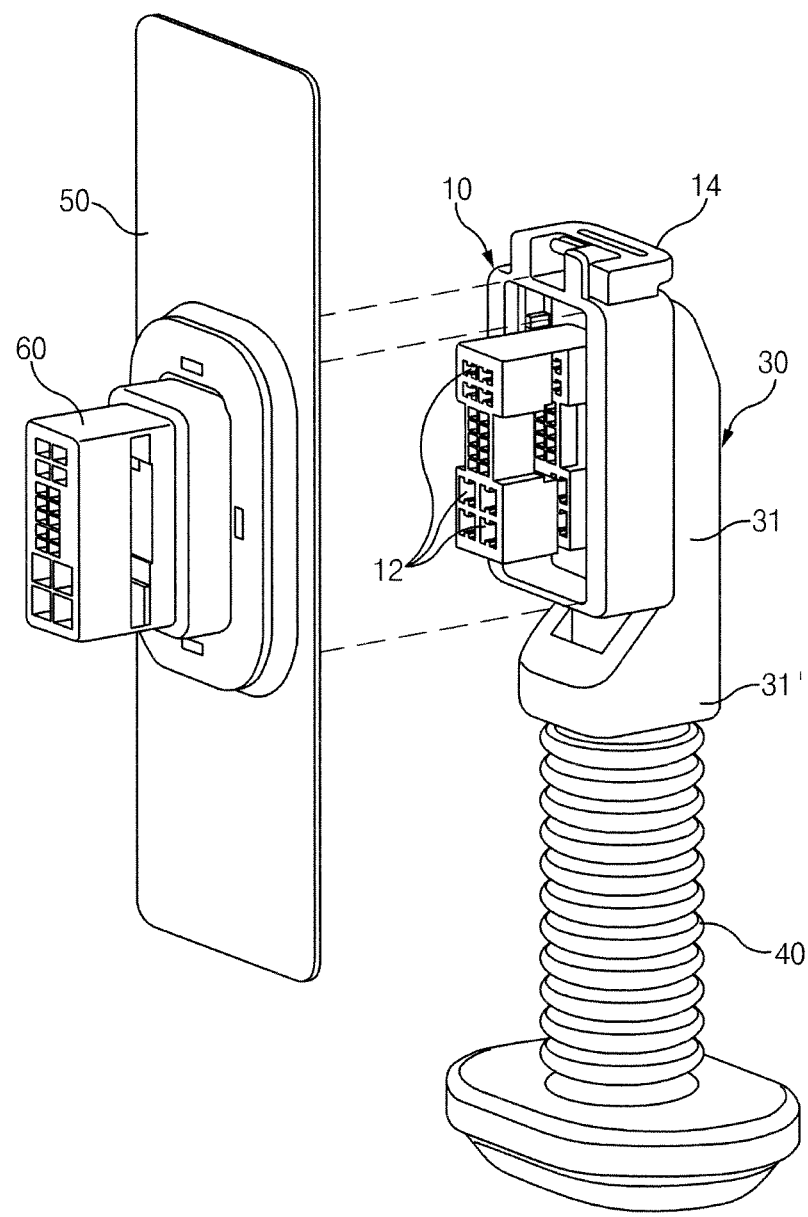
FIG. 6 is a perspective view illustrating a state before the connector for a door according to the exemplary embodiment of the present disclosure is coupled with a counter connector which is mounted in a panel.

In the above characteristics, as illustrated in FIG. 6, even though the connector for a door is coupled with the counter connector 60 which is mounted in the panel 50 of the vehicle, the protruding degree of the grommet 30 toward the rear of the housing 10 is relatively reduced and therefore space utilization is more facilitated.

As described above, according to the exemplary embodiments of the present disclosure, the housing and the connector for a door using the same according to the exemplary embodiments of the present disclosure may obtain the following effects.

According to the exemplary embodiments of the present disclosure, it is possible to extend the electric wire to the outside of the housing through an electric wire passing part which is formed from the rear end of the housing of the connector for a door toward the lateral direction of the housing. Therefore, the length of the electric wire extending toward the rear of the housing of the connector for a door is short and thus the overall length of the electric wire is relatively short, and as a result, the costs may be saved and the signal may be relatively accurately transferred.

Further, according to the exemplary embodiments of the present disclosure, the electric wire extends in the lateral direction of the housing through the electric wire passing part and thus comes out to the outside of the housing, and as a result, the protruding degree of the electric wire toward the rear of the housing may be minimized. Therefore, the protruding degree of the grommet enclosing the electric wire at the rear of the housing toward the rear of the housing may be reduced and thus the overall size of the connector for a door, more accurately, the length in the front and rear directions of the connector for a door may be relatively shorter.

Further, according to the exemplary embodiments of the present disclosure, the locking rib locked to the locking channel of the grommet does not constantly protrude from the rear surface of the housing and one side thereof is provided with the inclined part and even in the grommet, the locking channel locked to the locking rib is provided with the inclined part. Therefore, when the parallel parts of the locking rib are sequentially inserted into the parallel parts of the locking channel in the state in which the inclined part of the locking rib is inserted into the inclined part of the locking channel, the grommet may be easily mounted on the housing.

The spirit of the present disclosure has been illustratively described hereinabove. It will be appreciated by those skilled in the art that various modifications and alterations may be made without departing from the essential characteristics of the present disclosure. Accordingly, exemplary embodiments disclosed in the present disclosure are not to limit the spirit of the present disclosure, but are to describe the spirit of the present disclosure. The scope of the present disclosure is not limited to these exemplary embodiments. The scope of the present disclosure should be interpreted by the following claims, and it should be interpreted that all the spirits equivalent to the following claims fall within the scope of the present disclosure.

For example, it is not necessarily to use the electric wire guide cover 26. Further, the electric wire guide cover 26 has rigidity to some extent to maintain the shape of the grommet 30 as an original shape and serves to guide the electric wire, but when there is no need to perform the function, the electric wire guide cover 26 need not be used.

What is claimed is:

1. A housing forming a skeleton of a connector for a door coupled with a counter connector which is mounted in a panel, comprising:
   a terminal seating space penetrating through the housing back and forth and an electric wire seating space communicating with the terminal seating space to be opened to a rear of the housing; and
   an electric wire guide cover preventing the electric wire seating space from protruding backward so as to prevent a load from being applied to a grommet in which an electric wire is coupled with the housing,
   wherein a parallel part of a locking rib is parallel with a rear surface of the housing and an inclined part of the locking rib is inclined to the parallel part of the locking rib, and
   the parallel part of the locking rib includes first and second portions disposed at opposite sides of an inlet of the terminal seating space, and the inclined part of the locking rib connects the first and second portions of the parallel part of the locking rib to each other.

2. The housing according to claim 1, wherein the locking rib has a shape of a closed curve.

3. A housing forming a skeleton of a connector for a door coupled with a counter connector which is mounted in a panel, comprising:
   a terminal seating space penetrating through the housing back and forth and an electric wire seating space communicating with the terminal seating space to be opened to a rear of the housing,
   wherein the electric wire seating space is opened in a direction toward which the rear of the housing and one side of the housing face,
   a locking rib encloses an edge of an inlet of the terminal seating space, a portion opened to the rear of the housing is provided with a parallel part of the locking rib, and the edge of the inlet of the terminal seating space opened to the side of the housing is provided with an inclined part of the locking rib,
   the parallel part of the locking rib is parallel with a rear surface of the housing and the inclined part of the locking rib is inclined to the parallel part of the locking rib, and
   the parallel part of the locking rib includes first and second portions disposed at opposite sides of the inlet of the terminal seating space, and the inclined part of the locking rib connects the first and second portions of the parallel part of the locking rib to each other.

4. The housing according to claim 3, wherein a leading end of the inclined part of the locking rib is formed in a curved line.

5. The housing according to claim 3, wherein the locking rib has a shape of a closed curve.

6. A connector for a door, comprising:
   a housing provided with a terminal seating space in which a terminal is seated by penetrating through the housing back and forth and provided with an electric wire seating space communicating with the terminal seating space to be opened backward; and
   a grommet mounted on the housing to close the electric wire seating space of the housing to prevent external foreign materials from being entered into the electric wire seating space of the housing,
   wherein the electric wire seating space formed in the housing is opened in a direction toward which a rear of the housing and one side of the housing face,
   a locking rib encloses an edge of an inlet of the terminal seating space,
   a portion opened to the rear of the housing is provided with a parallel part of the locking rib and the edge of the inlet of the terminal seating space opened to the side of the housing is provided with an inclined part of the locking rib,
   the parallel part of the locking rib is parallel with a rear surface of the housing and the inclined part of the locking rib is inclined to the parallel part of the locking rib, and
   the parallel part of the locking rib includes first and second portions disposed at opposite sides of the inlet of the terminal seating space, and the inclined part of the locking rib connects the first and second portions of the parallel part of the locking rib to each other.

7. The connector for a door according to claim 6, wherein a leading end of the inclined part of the locking rib is formed in a curved line.

8. The connector for a door according to claim 6, wherein the electric wire seating space of the housing is further provided with an electric wire guide cover.

9. The connector for a door according to claim 8, wherein the electric wire guide cover is installed at a position corresponding to an opposite side of an electric wire extending part of the electric wire seating space of the housing to guide an electric wire in a direction of the electric wire extending part.

10. The connector for a door according to claim 6, wherein the grommet is configured of a rear end mounting part which is mounted on the rear surface of the housing and a side mounting part mounted on the one side of the housing,
   an edge of an inner side of an inlet corresponding to the rear end mounting part is provided with a parallel part of a locking channel to which the parallel part of the locking rib is locked, and an edge of an inner side of an inlet corresponding to the side mounting part is provided with an inclined part of the locking channel to which the inclined part of the locking rib is locked.

11. The connector for a door according to claim 10, wherein a front surface of the rear end mounting part of the grommet is parallel with the rear surface of the housing, and a front surface of the side mounting part of the grommet extends to be inclined to the front surface of the rear end mounting part of the grommet.

12. The connector for a door according to claim 6, wherein the locking rib has a shape of a closed curve.

* * * * *